(12) United States Patent
Tahi et al.

(10) Patent No.: US 6,358,279 B1
(45) Date of Patent: Mar. 19, 2002

(54) MINICAPSULORHEXIS VALVE

(75) Inventors: Hassan Tahi, Miami; Jean-Marie Parel, Miami Shores, both of FL (US); Pascal Chapon, Saint-Mande (FR)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 09/510,372

(22) Filed: Feb. 22, 2000

Related U.S. Application Data (60) Provisional application No. 60/121,179, filed on Feb. 22, 1999.

(51) Int. Cl.[7] .................................................. A61F 2/14
(52) U.S. Cl. ......................................... 623/4.1; 128/898
(58) Field of Search ........................... 623/4.1; 606/107; 128/898

(56) References Cited

U.S. PATENT DOCUMENTS

| | | |
|---|---|---|
| 4,033,349 A | 7/1977 | Baehr |
| 5,540,699 A | 7/1996 | Smith |

FOREIGN PATENT DOCUMENTS

| | | |
|---|---|---|
| EP | 0 328 117 A2 | 8/1989 |
| EP | 0 862 902 A2 | 9/1998 |
| FR | 2 698 264 | 5/1994 |
| WO | WO 89/07426 | 8/1989 |
| WO | WO 97/47247 | 12/1997 |

*Primary Examiner*—Dinh X. Nguyen
(74) *Attorney, Agent, or Firm*—Pillsbury Winthrop LLP (57) ABSTRACT

A mini capsulorhexis valve device is composed of a curved, flexible discoid flap-valve member shaped to align with an ocular lens capsular bag inner surface, and a curved, flexible retainer member shaped to align with an ocular lens capsular bag outer surface, the curved, flexible retainer member being attached at a fastening point to the curved, flexible discoid flap-valve member. Attachment of the curved, flexible discoid flap-valve member to the curved, flexible retainer member may be via bonding with a silastic adhesive. In a method of accessing an ocular lens, the mini capsulorhexis valve device establishes a portal controlling access to an ocular lens. The method may include inserting a cannula through the mini capsulorhexis valve device to permit removal of a crystalline lens matrix and replacement thereof with a capsular filling material. The method may also include injecting a cytotoxic agent into a lens capsule, during which leakage of the injected cytotoxic agent is prevented by the mini capsulorhexis valve device. The method may further include adjusting the refractive power of capsular filling material by adding or removing capsular filling material from the lens capsule during lens replacement surgery or post-surgically.

27 Claims, 5 Drawing Sheets

MINICAPSULORHEXIS VALVE

This application claims the benefit of U.S. Provisional Application No. 60/121,179, filed Feb. 22, 1999.

BACKGROUND OF THE INVENTION

1. Field of the Invention

The invention relates to a mini capsulorhexis valve device comprising a flexible discoid flap-valve member attached to a flexible retainer member, the device serving to seal a capsulorhexis opening created during ocular interventions.

2. Description of the Related Art

Figure 5:
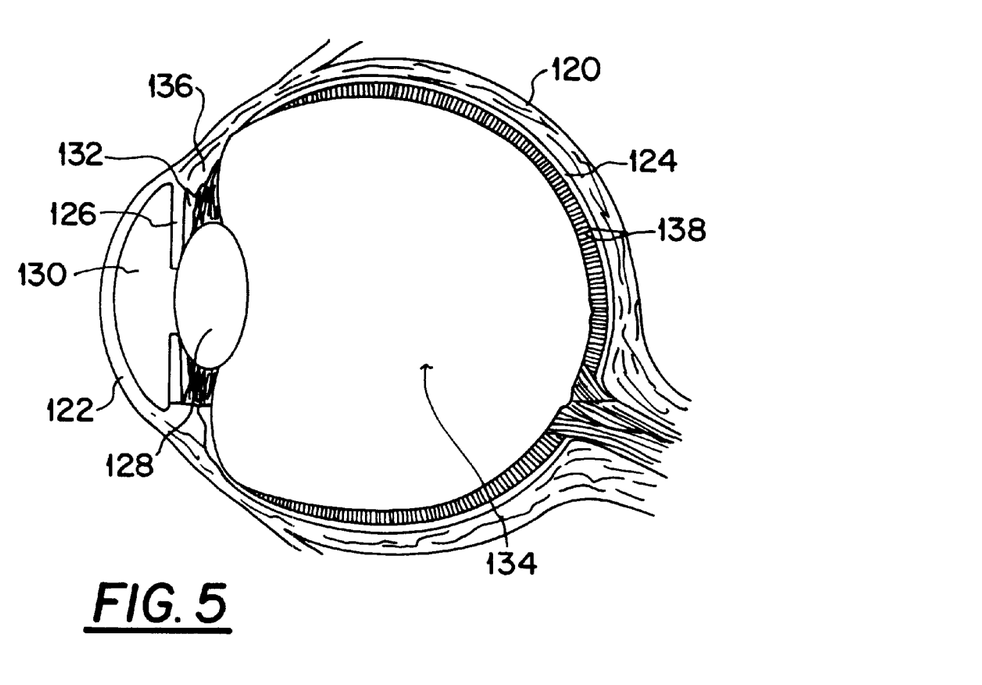
FIG. 5 depicts a horizontal section through a human eyeball.

The human eye, as depicted in FIG. 5, comprises a roughly spherical organ having essentially three distinct layers of tissue, divided into three basic chambers. The tough outer sclerotic coat 120 serves as a protective barrier for the eye, and forms the transparent cornea 122 through which light passes into the eye. The sclerotic coat 120 is composed of dense collagenous tissue. The middle choroid coat 124 forms the iris 126, a diaphragm that controls the amount of light admitted into the interior of the eye through the pupil. Immediately posterior to the iris 126 is the transparent crystalline lens 128, held in place by zonular fibers attached to ciliary processes surrounding the crystalline lens 128. The zonular fibers collectively culminate in the suspensory ligament of the lens. The region between the cornea 122 and crystalline lens 128 is denoted the anterior chamber 130 of the eye, whereas the gap created between portions of the crystalline lens 128 and iris 126 is known as the posterior chamber 132. Ciliary processes generate aqueous humor, which fills the anterior chamber 130 and posterior chamber 132. Aqueous humor provides for nutrient and metabolic exchange between the avascular cornea 122, crystalline lens 128, and iris 126. The posterior pole of the crystalline lens 128 abuts the hyaloid fossa of the posterior vitreous chamber 134 of the eye. Accommodation, the process of changing the focus of the eye between near and distant objects, is achieved by constriction and relaxation of the ciliary muscle 136 connected to the crystalline lens 128 via the zonular ligament. Such movement by the ciliary muscle 136 serves to shape the crystalline lens 128 to the appropriate optical configuration for focussing light rays from these objects onto the inner coat of the eye, structurally known as the retina 138.

The crystalline lens is a biconvex body, having an anterior convexity less steep and of a greater radius of curvature than its more parabolic posterior convexity. The lens is composed of elongated, prismatic cells known as lens fibers, which are tightly packed to form lamellar structures. Intracellular granular crystallins within the lens fibers confer upon the lens its transparent and refractive characteristics. Lens fiber structure and composition varies within the lens such that a firm central nucleus may be distinguished from a softer surrounding cortex. The entire lens is encompassed by the lens capsule (capsula lentis), a basement membrane into which the zonular fibers are inserted. The elastic lens capsule is composed of collagen fibers, glycosaminoglycans and glycoproteins. Due to its elastic properties, the lens capsule can stretch substantially in circumference without tearing.

A variety of disorders are known to impair or destroy normal function of the eye, including disorders of the lens, such as cataracts and presbyopia. Cataracts arise from progressive clouding of the crystalline lens, which, if left untreated, eventually obscures light rays from focussing on the retina. Historically, cataracts were surgically treated by either intracapsular removal of the entire lens structure, including the outer lens capsule and the inner crystalline lens matter, or extracapsular removal of the central portion of the anterior capsule and the crystalline lens matter, leaving in place the posterior lens capsule, known in the art as the ECCE procedure. These procedures are prone to complications, such as retinal detachment, and, in the case of extracapsular cataract extraction, opacification of the posterior capsule.

Recently developed lens refilling procedures may reduce the incidence of many complications associated with traditional cataract treatment modalities. One such procedure is disclosed in U.S. Pat. No. 4,002,169, in which a rotary masticating tool is introduced into the lens structure via an inserted hollow needle. The capsular tissue contents, including the cataract, lens cortex and lens nucleus, are physically liquefied and then withdrawn from the lens capsule via suction through the needle. Such a process leaves the lens capsule intact as a capsular bag within the posterior chamber. Often, a chemical treatment or sonication (phacoemulsification) is preferred over physical mastication for liquefying the lens. Following suction removal of the liquefied crystalline lens, the capsular bag may be flushed to remove remaining debris and then refilled with a molded synthetic lens, as disclosed in U.S. Pat. No. 5,674,282.

Alternatively, a new lens may be created in situ with a filler material having the appropriate characteristics to mimic the function of the natural crystalline lens. Many ophthalmic procedures designed to restore accommodation of the eye, such as lens refilling procedures for the correction of presbyopia and cataracts, rely on the replacement of endogenous lens matrix material with a transparent material of similar consistency and index of refraction and spectra.

Some of the preferred materials for filling the capsular bag comprise UV-curable polymers that require exposure to ultraviolet light to induce crosslinking. Such crosslinking typically requires two openings be created in the wall of the eye via bimanual surgery, which occupies both hands of the ophthalmic surgeon. Alternatively, crosslinking may be effected through the cornea, but such procedures may damage corneal tissues.

Intraocular lenses may comprise relatively hard materials, relatively soft materials, or a combination of both types of materials. For example, methyl methacrylates, polysulfones or other relatively hard, biologically inert optical materials may be used alone, or in combination with softer biologically inert silicones, hydrogels or semi-rigid thermolabile materials.

U.S. Pat. No. 5,391,590 discloses compositions useful as injectable intraocular lens material. Examples of polymerizable formulations include one or more polyorganosiloxanes having a vinyl functionality, a silicon-bonded hydride group, and the like. Such compositions may comprise soft, fast curing, low temperature vulcanization silicone gels capable of in situ polymerization within the capsular bag. High molecular weight, high viscosity silicone precursor fluids are preferred, as they are less likely to leak from the injection site prior to polymerization. Such high viscosity materials only require a low cross-linking density to achieve an elastic modulus similar to a human crystalline lens. However, a reduced cross-linking density of these polymers results in an unacceptable gummy product having low resilience.

Certain low viscosity, low molecular weight fluids have desirable properties upon cure for injectable ocular lenses, but readily leak from the injection site. Upon curing of leaked gel, a bump may form on the surface of a refilled capsule. Such bumps are known to irritate the iris and mediate corneal edema. In an attempt to overcome this limitation, suitable low molecular weight fluids may be pre-cured to induce polymerization prior to injection in to the lens capsular bag. Injection of such partially polymerized materials through a cannula may cause shear stress, which results in rough areas of the polymerized material that impair the function of the synthetic lens. Additionally, pre-cured polymer materials typically must be injected shortly after initiating crosslinking to prevent over-curing and reduced flow through the cannula, making such materials awkward to use.

Typically, the capsular bag tends to under fill unless very high density materials, such as gels having a viscosity of greater than 4 Mcts, are used. As mentioned hereinabove, viscous liquids and gels introduced into the capsular bag for this purpose often leak from the bag, particularly when fluids having less than 1 Mcts viscosity or soft gels are injected. Leakage of such materials into the anterior chamber of the eye may cause a number of ocular problems, and endanger delicate ocular structures. For example intraocular inflammation may be spurred by a foreign body reaction of the eye in response to the leaked material. Additionally, leaching of non-endogenous liquids or gels from the capsular bag may cause glaucoma, due to blockade of trabeculae and associated increases in intraocular pressure due to increased volumes of aqueous humor. Interference with motion of the iris and impairment of the optics of the eye due to glare are also known to occur upon escape of viscous liquids and gels introduced to the capsular bag.

Similarly, cataract surgery may require the introduction of a chemical agent to liquefy nuclear matter, and/or injection of a chemical or pharmacological agent to kill lens epithelial cells or impair their replication. Leakage of antimitotic compounds or hypoosmolar solutions destroys healthy, non-regenerative corneal endothelial and retinal cells of the eye, as opposed to the intended hypeiproliferative lens epithelium.

An anterior capsulotomy, specifically a capsulorhexis, is typically used to reduce some of the procedural and post-operative complications associated with extracapsular and lens refilling protocols. A continuous tear capsulorhexis involves preparing a circular or round capsulotomy in the anterior lens capsule, forming an essentially circular tear line substantially coaxial with the lens axis, in cases of ECCE and peripherally in the case of lens refilling, and removing the essentially circular portion of the anterior capsule delincated by the continuous tear line. Preferably, the capsulotomy is positioned within the zonule-free area of the anterior lens capsule. This type of capsulotomy forms a circular opening in the anterior lens capsule, through which cataractous lens matrix may be extracted by, for example, phacoemulsification and aspiration. What remains is a capsular bag having an elastic posterior capsule, an anterior capsular remnant about the anterior capsulotomy, and an annular capsular bag sulcus between the anterior capsule remnant and the outer circumference of the posterior capsule. Thus, the capsular bag remains attached to the surrounding ciliary muscle of the eye via the zonules, and is responsive to ciliary contraction and relaxation during accommodation.

Although continuous tear capsulorhexis is designed to provide an anterior capsule remnant or rim having a relatively smooth, continuous inner edge abutting the capsulotomy, the anterior rim is sometimes torn, radially sliced, or nicked during this procedure. Such damage to the anterior rim leaves the rim vulnerable to tearing radially when the rim is stressed, particularly upon insertion of instruments for manipulating the capsular lens matrix. Tearing of the lens capsule during capsulorhexis increases the likelihood of untoward leakage of materials injected into the evacuated capsular bag during lens refilling. To reduce the risk of such tearing, a deep anterior chamber is maintained throughout the surgery using a balanced salt solution or a viscoelastic material to fill the chamber. However, tears may arise despite taking such precautionary measures.

In an effort to address some of these ongoing problems in ophthalmic surgery, Nishi et al. (*Graefe's Arch Clin Exp Ophthamol* (1990) 228: 582–588) developed a new lens for small-incision surgery, which also serves to seal the capsular opening. Following a circular mini-capsulorhexis and phacoemulsification procedures, an acrylamide synthetic lens larger than the capsular opening is inserted into same. After injecting a visco-elastic material into the capsular bag and anterior chamber of the eye, the lens is inserted into the anterior chamber. The lens is then manipulated such that the lens is choked by the entire capsular margin along its circumference, thereby fixing the lens in place of the missing portion of anterior capsule. Since the lens seals the opening of the lens capsule, the lens capsular bag is capable of refilling. Thus, a replacement material, polyacrylamide gel, is injected into the capsular bag to expand the bag. Although generally successful, certain drawbacks exist with this process, including expansion of the capsulorhexis opening during filling, causing intraoperative leakage. Moreover, Nishi et al. reported difficulties achieving reproducible a centrally positioned circular capsulorhexis of an appropriate size for securely holding the inserted synthetic lens in the capsular bag. Furthermore, patients receiving, such intraocular lens implantation may develop capsular bag distention causing blurred vision.

Nishi and Nishi (*Arch Ophthalmol* (1998) 116(10): 1358–1361) recently devised a tube having a flange made to fit a surgically generated capsulorhexis opening in a patient's capsular bag. This tube is permanently bonded to the edges of the capsulorhexis with a silicone-based adhesive, meaning the device is an implant. Thereafter, a clear gel is injected through the tube via a 30 gauge stainless steel cannula. After filling the capsular bag, an adhesive within the tube seals the tube. The tube is then cut to remove excess length, although the remaining tube slightly protrudes from the bag into the anterior chamber of the eye. The protrusion of this implant may mechanically interfere with motion of the iris, impairing pupillary opening and closing. Contact of the inner surface of the iris causes drag, which may interfere with ocular accommodation. The protruding tube may scratch the corneal endothelium upon rubbing of the patient's eye containing the implant. Such implants are susceptible to biocompatibility problems, and may cause severe inflammatory reactions within the eye.

In view of the foregoing, a need clearly exists for a better means of safely introducing liquids and gels into a lens capsular bag during accommodation restoration procedures as well as certain forms of cataract therapy.

SUMMARY OF THE INVENTION

In a preferred embodiment of the invention, a mini capsulorhexis valve device comprises a curved, flexible discoid flap-valve member shaped to align with an ocular lens capsular bag inner surface, and a curved, flexible retainer member shaped to align with an ocular lens capsular bag outer surface, the curved, flexible retainer member being centrally or paracentrally attached at a fastening point to the curved, flexible discoid flap-valve member. Attachment of the curved, flexible discoid flap-valve member to the curved, flexible retainer member may be via bonding. Preferably, bonding is achieved via a silastic adhesive.

The mini capsulorhexis valve device may have a curved, flexible discoid flap-valve member comprising a circular disc having a thickness ranging from about 10 micrometers to about 100 micrometers, depending upon the material used to produce the device. Preferably, the flexible discoid flap-valve member has a thickness ranging between about 50 micrometers to about 90 micrometers. The mini capsulorhexis valve device may also have a curved, flexible discoid flap-valve member comprising a diameter between about 1.0 mm to about 2.4 mm, preferably ranging from about 1.4 mm to about 2.2 mm. The curved, flexible retaining member comprises a band having a thickness of about 30 micrometers to about 100 micrometers, preferably ranging from about 50 micrometers to about 90 micrometers. The curved flexible retaining member may be formed in a rectangle, crescent, "V" or other suitable shape. The mini capsulorhexis valve device may have a curved, flexible retaining member comprising a length ranging from about 3.0 mm to about 4.0 mm and a width ranging from about 0.30 mm to about 0.40 mm.

In another preferred embodiment, the mini capsulorhexis valve device has a curved. flexible retaining member about 3.4 mm in length and about 0.36 mm in width.

Preferably, the mini capsulorhexis valve device comprises at least one flexible biocompatible elastomeric material. The elastomeric material may comprise a synthetic polymer or a polymer of biological origin. For example, the biocompatible elastomeric material may comprise polymer of biological origin, such as a collagen, a collagen-derivative, or mixtures thereof. The biocompatible elastomeric material may comprise at least one synthetic polymer selected from the group consisting of a urethane, a silicone, a crosslinkable terminated trimethyl polydimethylsiloxane, and a crosslinkable terminated dimethyldiphenylsiloxane. More preferably, the biocompatible elastomer comprises a 50 to 80 shore A durometer medical grade crosslinkable trimethyl polydimethylsiloxane. Even more preferably, the biocompatible elastomer comprises a biodegradable material, for example, a material capable of biodegradation upon photoactivation. Preferably, the mini capsulorhexis valve device comprises an elastomer that is transparent to UV radiation of about 300 nm–400 nm wavelength to allow photocrosslinking of materials, for example, gels or sols, through the mini capsulorhexis valve device. Also preferred is a mini capsulorhexis valve device may comprising a gel crosslinkable by visible light of about 400 nm–700 nm or near infrared light of about 700 nm–1100 nm.

In another preferred embodiment, the mini capsulorhexis valve device comprises an implantable device that remains in place for an extended period of time, or a disposable device. Preferably, implantable mini capsulorhexis valve devices comprise a biodegradable biocompatible elastomer.

In yet another embodiment, a method of accessing an ocular lens is provided, comprising making a limbus incision to open an anterior chamber of an eye and filling the anterior chamber with a viscoelastic solution. Thereafter, an anterior capsulorhexis opening is created in a lens capsule, into which is inserted a mini capsulorhexis valve device having a flexible flap-valve member and a flexible retaining member. The mini capsulorhexis device is inserted such that said flexible flap-valve member is positioned along an interior surface of the lens capsule and said flexible retaining member is positioned along an outer surface of the lens capsule, compressing a wall of the lens capsule therebetween. The mini capsulorhexis valve device is then released to establish a portal controlling access to an ocular lens. The method may further comprise inserting a cannula through the mini capsulorhexis valve device to permit removal of a crystalline lens matrix and replacement thereof with a capsular filling material.

Still another embodiment is a method of accessing an ocular lens in which a mini capsulorhexis valve device prevents leakage of antimitotic or cytotoxic agents during refilling of a capsular bag.

BRIEF DESCRIPTION OF THE DRAWINGS

In the accompanying drawings:

FIG. 3a shows a sagittal view of a lens capsule having a mini capsulorhexis valve device closing a hole therein, through which a cannula is inserted into the lens capsule;

FIG. 3b shows an enlarged detail of a top plan view of FIG. 3a;

FIG. 3c shows an enlarged view of the detail of FIG. 3a;

FIG. 4b shows a top plan view of a capsulorhexis of a lens capsule scaled by a mini capsulorhexis valve device as depicted in FIG. 4a;

DETAILED DESCRIPTION OF THE DRAWINGS

The configuration of the inventive mini capsulorhexis device is described in detail below. Parts or features common to more than one Figure are labeled with the same reference numeral throughout the Figures for consistency.

Figure 1A:
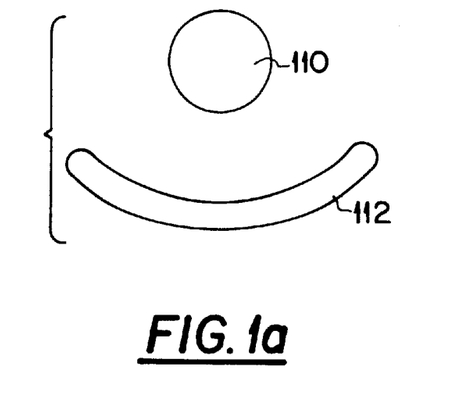
FIG. 1a shows an exploded view of the mini capsulorhexis valve device.
Figure 1B:
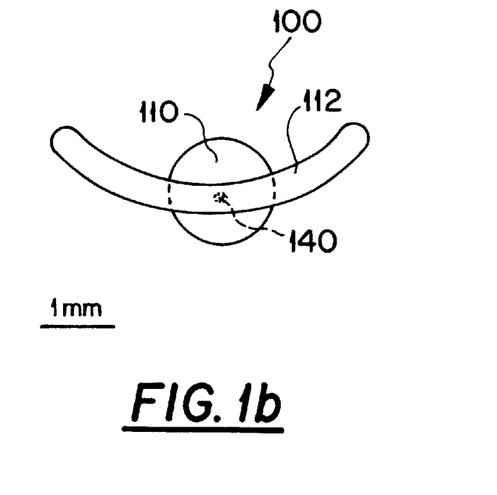
FIG. 1b shows a top plan view of the minicapsulorhexis device having a flexible retaining member comprising a band in a crescent shape.
Figure 2:
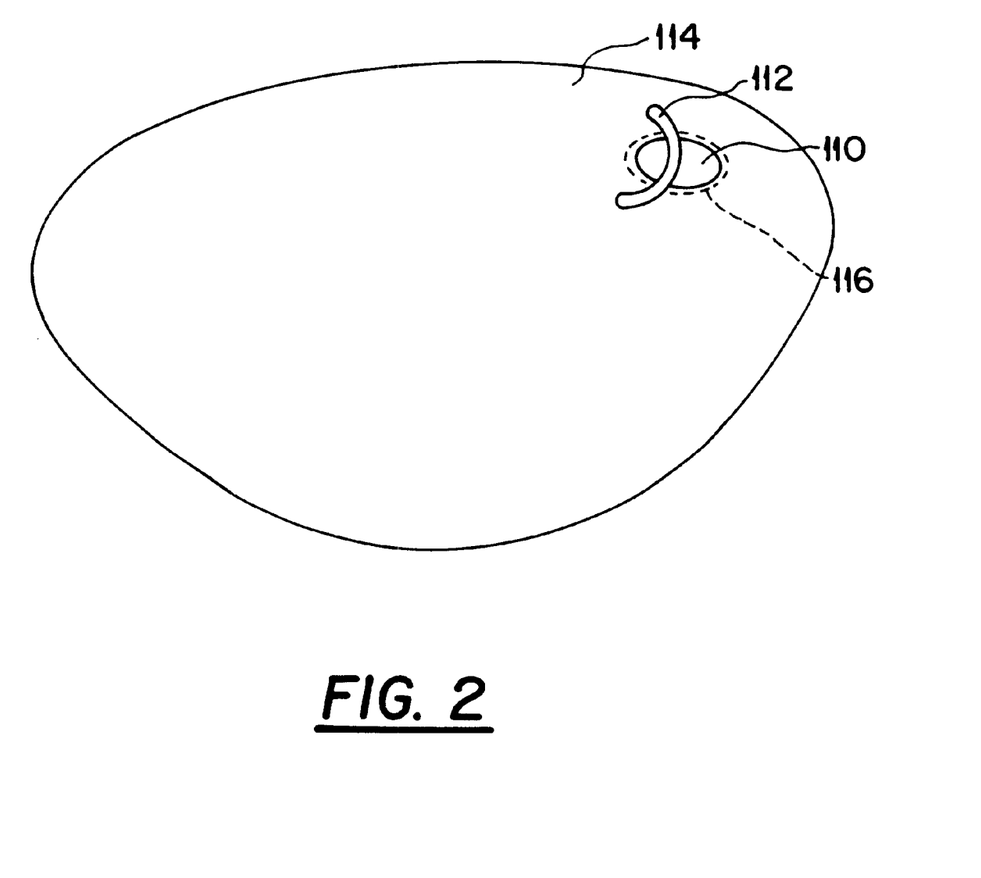
FIG. 2 shows the mini capsulorhexis valve device inserted into the capsular bag of an eye.
Figures 3A, 3C:
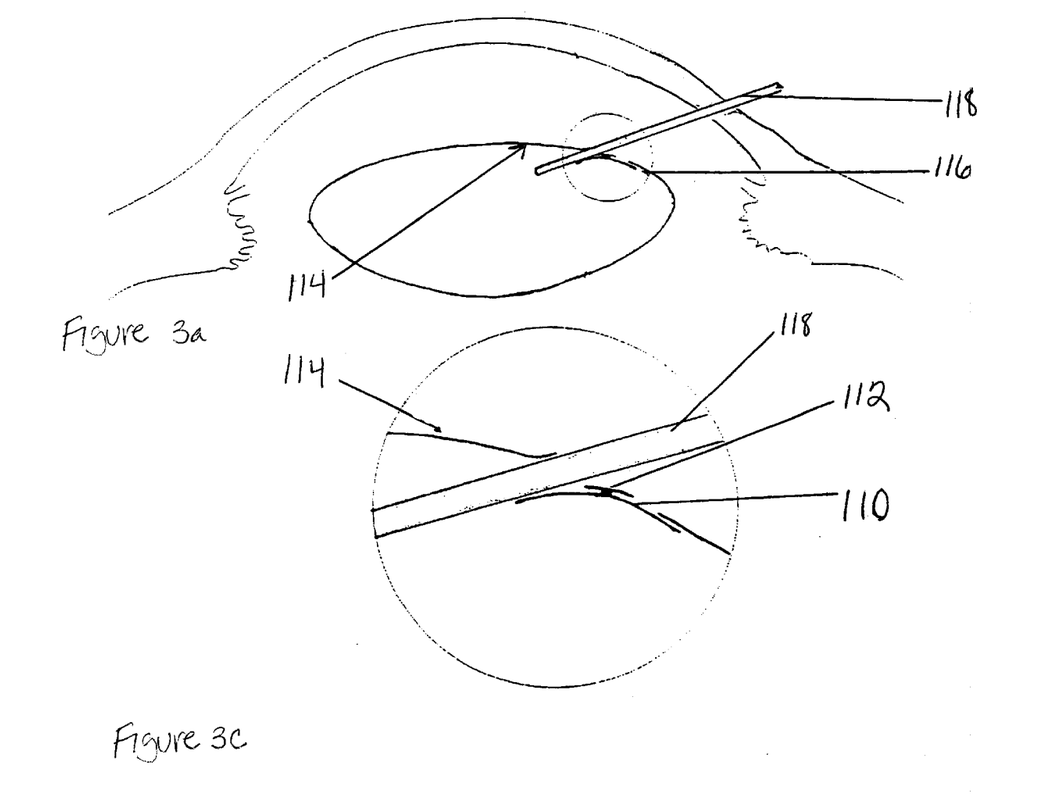
Figure 3B:
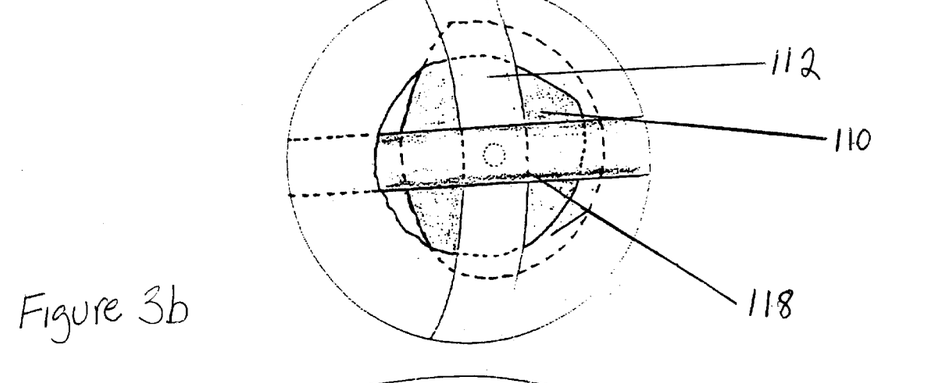

In a preferred embodiment of the invention, a mini capsulorhexis valve device 100 comprises a flexible discoid flap-valve member 110 paracentrally attached at a fastening point 140 to the surface of a flexible retainer member 112, as illustrated in FIGS. 1a and 1b. However, the fastening point 140 may be centrally located on the flexible discoid flap-valve member 110, although this configuration may restrict the movement of instruments inserted through the mini capsulorhexis valve device 100. As shown in FIG. 2, upon insertion into a capsulorhexis opening in the anterior capsule of the eye 114, flexible discoid flap member 110 is oriented at least partially within the anterior capsule 114, while flexible retainer member 112 is situated exterior to the anterior capsule 114 such that the anterior capsule wall 116 is disposed therebetween. Flexible discoid flap valve member 110 is selected to be slightly larger than the capsulorhexis opening to fill the void of the opening, while the length of the flexible retainer member 112 is larger than the capsulorhexis preferably about twice as large. Flexible retainer member 112 serves as a mechanical brace to support the flexible discoid flap valve member 110. Preferably, the flexible discoid flap valve member 110 has a curved shape to align with the capsular bag inner surface, and the flexible retainer member 112 is curved to align with the capsule outer surface. In addition, the flexible retainer member 112 is arched in a vertical dimension to avoid mechanical interference with the iris. The mini capsulorhexis valve device 100 prevents fluid or gel leakage from the capsular bag when inserting a cannula 118 between the flexible discoid flap valve member 110 and flexible retainer member 112 into the bag, as illustrated in FIGS. 3a, 3b and 3c. Upon insertion, cannula 118 is compressed between the flexible anterior capsular wall 116 of the anterior capsule 114 and the mini capsulorhexis valve device 100.

Figure 1C:
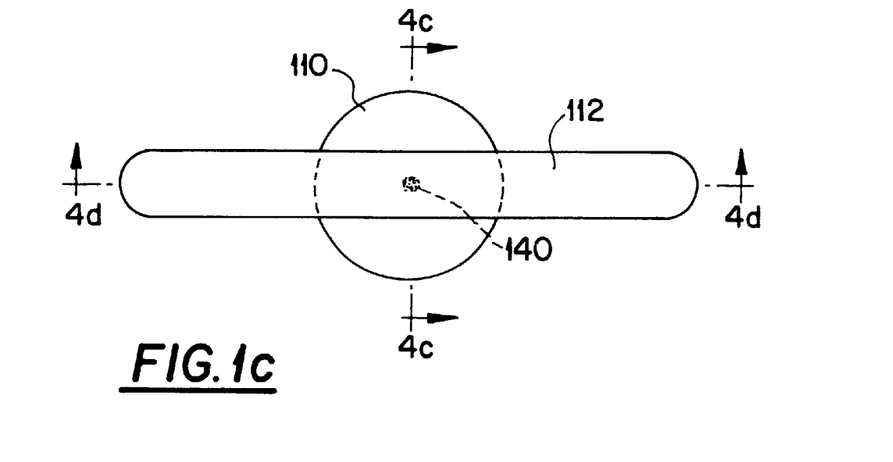
FIG. 1c shows a top plan view of the minicapsulorhexis device having a flexible retaining member comprising a band in a rectangular shape.
Figure 1D:
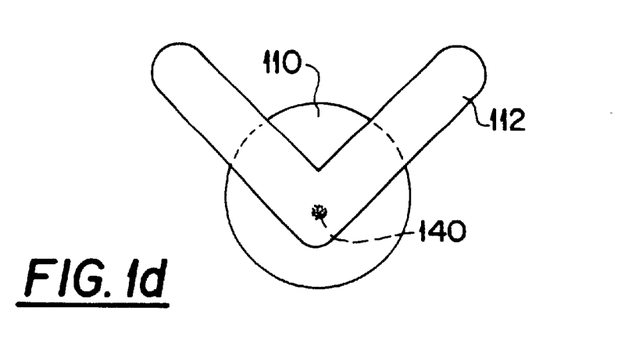
FIG. 1d shows a minicapsulorhexis device having a flexible retaining member comprising a band in a v-shape.
Figure 4A:
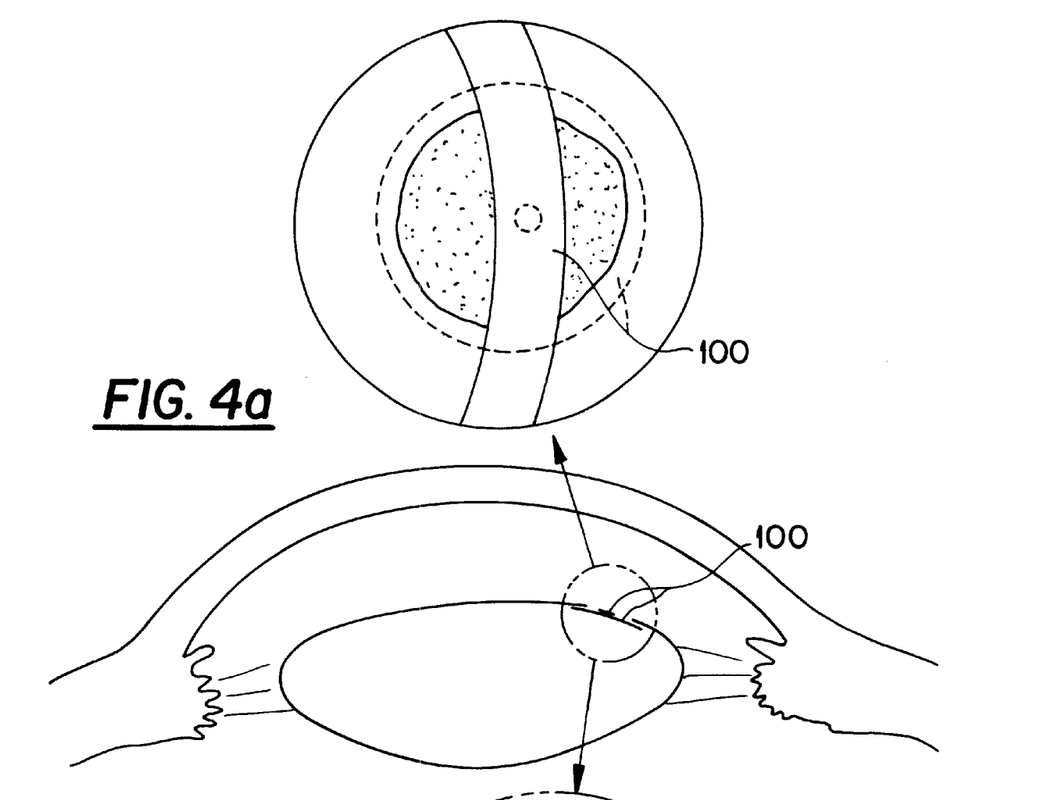
FIG. 4a shows a sagittal view of a lens capsule having a mini capsulorhexis valve device closing a hole in the capsulorhexis of the lens capsule.
Figure 4B:
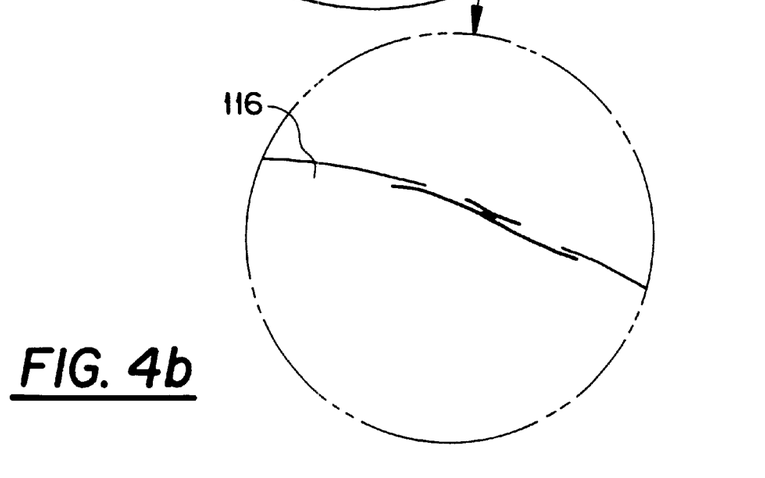
Figure 4C:
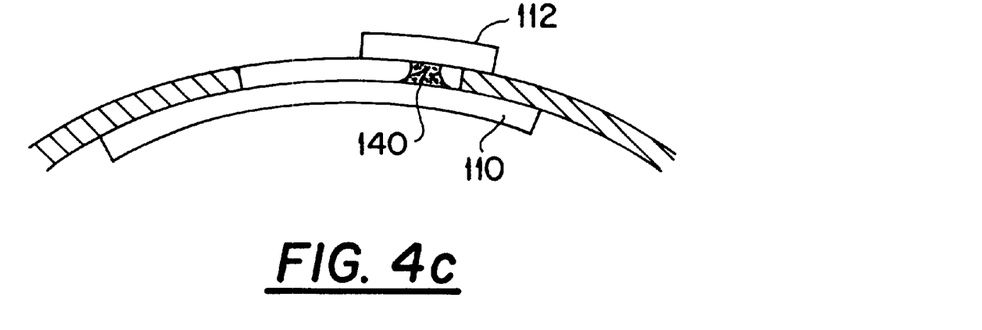
FIG. 4c is an enlarged view showing the subject matter of FIG. 4a in greater detail, with the mini capsulorhexis valve device shown as a section through line 4c—4c of FIG. 1c.
Figure 4D:
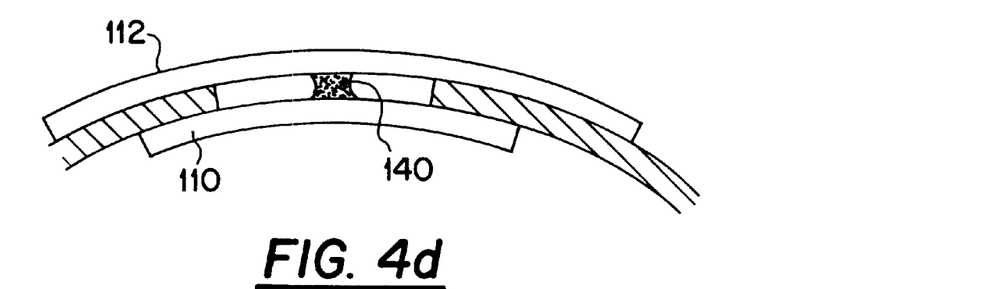
FIG. 4d is an enlarged view similar to that of FIG. 4c, with the mini capsulorhexis valve device shown as a section through line 4d—4d of FIG. 1c.

Upon removal of cannula 118, the mini capsulorhexis valve device 100 compresses the anterior capsular wall 116 to seal the capsular bag, trapping injected fluids or gels in the bag, as shown in FIGS. 4a–d. FIGS. 4c and 4d are detail views of the subject matter of FIGS. 4a and 4b. In FIGS. 4c and 4d, the capsulorhexis valve 100 is shown sectionally through lines 4c—4c and 4d—4d, respectively, of FIG. 1c. Sealing the capsule opening from the surrounding environment enables, for example, safer and more efficient endocapsular treatment modalities, such as the introduction of antiproliferative or cytotoxic compounds to impair epithelial proliferation in cataract patients. Thus, introduction of antiproliferative or cytotoxic agents, such as 5-fluorouracil, according to the invention may prevent postoperative capsular opacification. The mini capsulorhexis valve device 100 also permits the endolavage of dead cells and debris from the capsule. Additionally, the mini capsulorhexis valve device 100 allows the safe injection of a UV curable polymer into the capsule and subsequent in situ crosslinking by directed exposure to UV light by a fiber optic UV source inserted into the eye through the mini capsulorhexis valve device 100.

Capsular filling material may be added or removed via injection or aspiration through the mini capsulorhexis valve device 100 to adjust the refractive power of the capsular filing material. Adjustment of the refractive power of the de nuovo lens formed from the capsular filing material may be accomplished during lens replacement surgery, or at some point in time after surgery if an implantable mini capsulorhexis valve device 100 is used.

Following insertion, the mini capsulorhexis valve device 100 may optionally be removed from the eye. Removal would be desirable when, for example, a lens refilling procedure is completed and no further manipulation of the lens capsule is anticipated.

To fit the different sizes of capsulorhexis openings, typically about 0.7 mm to about 1.5 mm in diameter in the peripheral capsular bag, the mini capsulorhexis valve device 100 is engineered to a variety of dimensions. Preferably, the flexible discoid flap valve member 110 is a thin circular disc having a thickness of about 10 micrometers to about 100 micrometers. preferably about 30 micrometers to about 50 micrometers. Likewise, the flexible retaining member 112 comprises a very thin rectangular, crescent shaped, "v"-shaped or similarly configured band, having a thickness of, preferably, about 30 micrometers to about 100 micrometers, more preferably about 50 micrometers to about 90 micrometers. The flexible discoid flap valve member 110 diameter may range from about 1.0 mm to about 2.4 mm, preferably from about 1.4 mm to about 2.2 mm, while the flexible retaining member 112 may range from about 3.0 mm to about 4.0 mm in length and from about 0.30 to about 0.40 mm in width. A preferred flexible retainer member 112 has the dimensions of about 3.4 mm length by 0.36 mm width. The diameter of a surgical capsulorhexis opening may be assessed using a micro-ruler placed against a patient's cornea, or by using an intraocular gauge. Intraocular gauges are typically round, smooth, pin-like devices having length marks thereon, suitable for direct placement against the lens capsule surface. Measurement errors of about 10% may be incurred due to corneal refractive power, depending upon the location of the capsulorhexis in relation to the cornea, as well as the positioning of the ruler on the cornea (parallax). Errors are minimized when using the aforementioned intraocular gauge.

The discoid flap valve member 110 and the flexible retainer member 112 are preferably curved to fit the quasi-spherical shape of the capsule inner and outer surface. Tile flexible retainer 112 is arciform in shape to avoid the iris. Shaping of the discoid flap valve member 110 and the flexible retainer member 112 may be achieved using molding jigs. Insertion of the mini capsulorhexis valve device 100 is accomplished employing toothless, smooth jaw microforceps. Care must be taken to preventmicrobial or foreign particulate contamination of the mini capsulorhexis valve device 100 during manipulation.

Typically, a flexible discoid flap valve member 110 is attached at a fastening point 140 to a rectangular or crescent-shaped flexible retainer member 112. Preferably the fastening point 140 is centrally or paracentrally located on the flexible discoid flap valve member 110. Any suitable fastening means may be used to affix the two members. A preferred means of attachment is bonding via a silastic adhesive. A molded single piece mini capsulorhexis valve device 100 in which the flexible discoid flap member is integrally attached to the flexible retainer member is contemplated.

Both the flexible discoid flap valve member 110 and the flexible retainer member 112 of a mini capsulorhexis valve device 100 may be constructed from flexible, biocompatible elastomer. Examples of suitable elastomeric materials include thin silicone membranes cast in a laminar flow hood using a 50 shore A durometer silicone (Eccosil #4553, Emerson & Cumming, Inc., Canton, Mass., USA), and a medical grade crossslinked trimethyl-polydimethylsiloxane (Silastic® silicone elastomer, Dow Corning, Midland, Mich., USA). Collagen, collagen derivatives or combinations thereof are also contemplated as suitable biocompatible elastomers. For a disposable mini capsulorhexis valve device 100. medical grade polymeric materials such as urethane, crosslinkable trimethyl terminated polydimethylsiloxanes, and crosslinkable trimethyl terminated dimetlayldiphenylsiloxanes may be employed. Mini capsulorhexis valve devices may be manufactured via conventional casting and molding processes, particularly via injection molding.

A flexible flap valve member may remain as an implant within the capsular bag under certain circumstances. Such circumstances include, inter alia, the injection into the capsular bag of a gel designed not to fully polymerize, introduction of a gel which was intended to but failed to fully crosslink upon curing, and introduction of a viscous liquid or gel that firmly sticks to the mini capsulorhexis valve device. Implantable mini capsulorhexis valve devices comprise biocompatible implant grade materials. After implantation of a mini capsulorhexis valve device and injection therethrough of a capsular filling material, the flexible retainer member is severed from the flexible flap valve member, typically usingmicroscissors, and the severed flexible retainer member is removed from the eye.

The physicochemical properties of the material to be injected into the capsular bag will influence the choice of material for a given mini capsulorhexis valve device. The mini capsulorhexis valve device must comprise a material that will not adhere to viscous fluid or gel injected therethrough. For example, hydrophilic gels such as UV-curable hydrogels, are compatible with a mini capsulorhexis valve device manufactured from a hydrophobic material, such as polydimethylsiloxane (PDMS). By contrast, a mini capsulorhexis valve device comprising hydrophilic material, such as a methyl acrylate (polyHEMA), is preferred for injection of a hydrophobic fluid or gel into the capsule.

Mini capsulorhexis valve devices designed for the introduction of UV crosslinkable polymers into the capsular bag may comprise elastomeric materials transparent to UV radiation in the 300–400 nm wavelength range to allow photocrosslinking of materials, such as gels, through the mini capsulorhexis valve. Also preferred is a mini capsulorhexis valve device comprising a crosslinkable material, such as a gel or gel-like substance, crosslinkable by visible light of about 400 nm–700 nm or near infrared light of about 700 nm–1100 nm. Such transparent materials permit in situ crosslinking of polymeric materials through the mini capsulorhexis valve device, thereby avoiding corneal damage from exposure to radiation.

Any material selected for either a disposable or implantable mini capsulorhexis valve device must be capable of withstanding sterilization procedures. Known procedures include sterilization by autoclaving, gamma irradiation, and ethylene oxide gas.

Ocular surgical procedures utilizing the inventive mini capsulorhexis valve device are safer and more efficient than procedures using conventional methods. The mini capsulorhexis valve device closes a capsular incision or fissure intraoperatively, permitting injection of toxic therapeutic agents, viscous fluids and gels into the capsular bag without leakage. Capsular lavage with antimitotic agents after placement of the mini capsulorhexis valve device may reduce postoperative problems associated with cataract surgery, such as opacification and edema. Closing of incisions with mini capsulorhexis valve devices enables control of intracapsular pressure and volume during lens refilling procedures. Pressurization of the capsular bag to levels greater than physiological intraocular pressure may be achieved using the inventive mini capsulorhexis valve device to ensure complete filling of the capsular bag. Implantation of a mini capsulorhexis valve device will permit adjustments to be made in lens filling material volume in response to accommodation. Closing capsular holes by placement of mini capsulorhexis valve devices therein avoid postoperative complications generated by under filled bags, such as, inter alia, hyperopic shift, folds in the posterior capsule, space for lens epithelial cell proliferation and fibrosis.

Reduced radiation levels may be used in connection with the inventive mini capsulorhexis valve device to crosslink materials more slowly than with traditional ocular treatment modalities. Ophthalmic surgeons need only a single incision and use of one hand to insert the mini capsulorhexis valve devices. Once the mini capsulorhexis valve device is seated, all further intraocular manipulations may be accomplished using one hand, including injection of fluids and gels into the capsular bag, irradiation of crosslinkable filler materials with a fiber optic light source, and the like. No interference with iris motion occurs when using mini capsulorhexis valve devices because the inventive devices essentially eliminate protrusion of crosslinked gel. Additionally, the inventive mini capsulorhexis valve devices permit lavage of the anterior chamber and permit the easy removal of small air bubbles from the capsular bag.

Procedures designed to refill the eye lens, correct presbyopia, and treat cataracts may be improved when conducted using mini capsulorhexis valve devices according to the invention. Further uses of the inventive mini capsulorhexis valve devices include use as temporary patches for small corneal perforations as well as patches to fill perforations in no-ocular structures, such as organs and blood vessels.

The invention will be further illustrated by the following non-limiting example.

EXAMPLE

A small peripheral corneoscleral incision approximately 2 mm wide was made at the limbus to open the anterior chamber of the eye of each test subject in a collective group of anesthetized New Zealand White rabbits. Test animals were 2 months old, weighing about 1 kilogram each. Anesthesia comprised 14 mg/Kg body weight ketamine together with 7 mg/Kg body weight xylazine. The anterior chamber was subsequently filled with a viscoelastic solution, such as 1% sodium hyaluronate, to maintain anterior chamber depth and to protect the delicate corneal endothelium. A small round capsulorhexis opening of about 0.8 mm to 1.2 mm in diameter was created at the periphery of the anterior surface of the crystalline lens. The capsular bag was evacuated of its contents, and cleaned using standard instrumentation (Phaco-Ersatz MPA, U.S. Pat. No. 5,613,972; and mini IA, See American Journal of Ophthalmology 1986, Vol. 102, pp. 91–94) Using fine forceps, the mini capsulorhexis valve device was inserted into the eye and positioned such that the flexible round flap valve member was located within the bag, and, after manipulating its right and left arms into position, the flexible retaining member was situated outside of the bag. Both members therefore sandwiched the capsule walls. The device was released immediately upon insertion to close off the inner capsular volume from the anterior and posterior chambers.

Lavage via infusion-aspiration of the capsular bag was accomplished by inserting a thin, 22–30 gauge cannula above the retainer member and between the lens capsule and the flap valve member, wherein the cannula tip extended to a certain length within the capsular bag. As endocapsular pressure increased, the flexible flap valve member tightly closed the capsulorhexis opening, the surface of the flexible flap valve member intimately abutting the lower surface of the cannula, such that the upper surface of the cannula intimately abutted the inner capsular wall. This configuration effectively sandwiched the cannula between the flexible flap valve member and the inner capsular wall. The flexible retainer member maintained the flap valve member in position as the cannula tip was moved within the capsular bag during the lavage procedure.

Removal of the cannula closed the flap valve, trapping the injected fluid in the capsular bag. Following lavage (i.e.

photodynamic treatment (PDT) of the lens epithelium), wash fluid was easily removed from the capsular bag by aspiration. Once all of the fluid contained in the bag was removed, the posterior capsule collapsed against the anterior capsule and the flexible flap valve member. Lens refilling was thereafter achieved by injection of a pre-selected polymer into the capsular bag via a cannula similar in size to the cannula used for lavage. Alternatively, an infusion/aspiration double cannula could have been used as well.

Upon completion of lens filling, the flap valve member closed the capsulorhexis opening and the capsular bag shaped the injected polymer. The surgeon performing the procedure assessed the capsular bag volume by viewing the capsular bag through a microscope, and adjusted the volume by injecting or aspirating polymer therefrom as needed. As the flap valve sealed the capsular bag, the polymer within the bag was irradiated in situ by insertion of a fiber optic probe through the same corneoscleral opening used to inject the anterior chamber. The radiant energy emitted from the fiber optic probe was transmitted through the flexible retainer member and flexible flap valve member, thereby curing the polymer in the capsular bag.

After polymerization of the polymer located in the capsular bag behind and around the flexible flap valve member, the entire mini capsulorhexis valve device was removed from the eye using fine forceps. Manual aspiration and lavage was then performed to remove the viscoelastic material maintaining the anterior chamber depth. A single stitch was used to close the corneoscleral incision in each rabbit's eye. No stitches will be necessary upon conducting the procedure in human patients due to a slight difference in the anatomy of rabbit eyes from that of human eyes. Tests on human cadaver eyes have ascertained the practicality of inserting and removing the inventive mini capsulorhexis valve device in human eyes.

The foregoing detailed description of the embodiments of the invention, although preferred, is provided for illustrative purposes and is not intended to limit the scope of the invention. Obviously, one skilled in the art may envision modifications that fall within the spirit and scope of the following claims and their equivalents.

What is claimed is:

1. A mini capsulorhexis valve device comprising
a curved, flexible discoid flap-valve member shaped to align with an ocular lens capsular bag inner surface, and
a curved, flexible retainer member shaped to align with an ocular lens capsular bag outer surface, said curved, flexible retainer member being attached at a fastening point to said curved, flexible discoid flap-valve member.

2. The mini capsulorhexis valve device according to claim 1, wherein said curved, flexible discoid flap-valve member comprises a circular disc having a thickness ranging from about 10 micrometers to about 100 micrometers.

3. The mini capsulorhexis valve device according to claim 2, wherein said curved, flexible discoid flap-valve member comprises a circular disc having a thickness ranging from about 30 micrometers to about 50 micrometers.

4. The mini capsulorhexis valve device according to claim 2, wherein said curved. flexible discoid flap-valve member has a diameter ranging from about 1.0 mm to about 2.4 mm.

5. The mini capsulorhexis valve device according to claim 4, wherein said curved, flexible discoid flap-valve member has a diameter ranging from about 1.4 mm to about 2.2 mm.

6. The mini capsulorhexis valve device according to claim 1, wherein said fastening point is centrally or paracentrally attached to said curved, flexible discoid flap-valve member.

7. The mini capsulorhexis valve device according to claim 1, wherein said curved, flexible retaining member comprises a band having a thickness ranging from about 30 micrometers to about 100 micrometers, said band having a shape selected from the group consisting of rectangular, crescent-shaped and V-shaped.

8. The mini capsulorhexis valve device according to claim 7, wherein the band thickness ranges from about 50 micrometers to about 90 micrometers.

9. The mini capsulorhexis valve device according to claim 7, wherein said curved flexible retaining member has a length ranging from about 3.0 mm to about 4.0 mm and a width ranging from about 0.30 mm to about 0.40 mm.

10. The mini capsulorhexis valve device according to claim 9, wherein said curved, flexible retaining member is about 3.4 mm in length and about 0.36 mm in width.

11. The mini capsulorhexis valve device according to claim 1, wherein said mini capsulorhexis valve device comprises at least one flexible biocompatible elastomer.

12. The mini capsulorhexis valve device according to claim 11, wherein said biocompatible elastomer comprises a synthetic polymer or a polymer of biological origin.

13. The mini capsulorhexis valve device according to claim 12, wherein said polymer of biological origin comprises collagen.

14. The mini capsulorhexis valve device according to claim 12, wherein said synthetic polymer comprises at least one synthetic polymer selected from the group consisting of urethanes, silicones, crosslinkable terminated trimethyl polydimethylsiloxanes, and crosslinkable terminated dimethyldiphenylsiloxanes.

15. The mini capsulorhexis valve device according to claim 14, wherein said at least one synthetic polymer comprises a 50 shore A durometer medical grade crosslinkable trimethyl polydimethylsiloxane.

16. The mini capsulorhexis valve device according to claim 14, wherein said elastomer is transparent to radiation of a wavelength selected from the group consisting of about 300 nm to about 400 nm, about 400 nm to about 700 nm and about 700 nm to about 1100 nm.

17. The mini capsulorhexis valve device according to claim 1, wherein said mini capsulorhexis valve device comprises an implantable device.

18. The mini capsulorhexis valve device according to claim 17, wherein said implantable device comprises a biodegradable biocompatible elastomer.

19. The mini capsulorhexis valve device according to claim 1, wherein said mini capsulorhexis valve device comprises a disposable device.

20. The mini capsulorhexis valve device according to claim 1, wherein said curved, flexible discoid flap-valve member is bonded to said curved, flexible retainer member.

21. The mini capsulorhexis valve device according to claim 20, wherein bonding is achieved via a silastic adhesive.

22. A method of accessing an ocular lens, comprising:
making a limbus incision to open an anterior chamber of an eye;
filling said anterior chamber with a viscoelastic solution;
creating an anterior capsulorhexis opening in a lens capsule;
inserting a mini capsulorhexis valve device having a flexible flap-valve member and a flexible retaining member into said capsulorhexis opening, such that said flexible flap-valve member is positioned along an interior surface of the lens capsule and said flexible retaining member is positioned along an outer surface of the lens capsule, compressing a wall of the lens capsule therebetween; and releasing said mini capsulorhexis valve device to establish a portal controlling access to an ocular lens.

23. The method according to claim 22, further comprising inserting a cannula through said mini capsulorhexis valve device into the lens capsule to permit removal of a crystalline lens matrix and replacement thereof with a capsular filling material.

24. The method according to claim 23, further comprising injecting a cytotoxic or antiproliferative agent into the lens capsule, wherein said mini capsulorhexis valve device prevents leakage of said injected cytotoxic or antiproliferative agent.

25. The method according to claim 24, wherein the flexible discoid flap-valve member has a diameter of about 6 mm.

26. The method according to claim 23 further comprising adjusting capsular filling material refractive power by adding or removing capsular filling material from the lens capsule.

27. The method according to claim 26, wherein the capsular filling material refractive power is adjusted during lens replacement surgery or after lens replacement surgery.

* * * * *